(12) United States Patent
Bach et al.

(10) Patent No.: US 8,690,849 B2
(45) Date of Patent: Apr. 8, 2014

(54) BODY WASTE COLLECTING DEVICE

(75) Inventors: Anders Bach, Kobenhavn S (DK);
Esben Stroebech, Hoersholm (DK);
Mads Lykke, Broenshoej (DK); Astrid Toftkaer, Soeborg (DK); Hasse Buus, Humlebaek (DK); Tom Kongebo, Humlebaek (DK)

(73) Assignee: Coloplast A/S, Humlebaek (DK)

(*) Notice: Subject to any disclaimer, the term of this patent is extended or adjusted under 35 U.S.C. 154(b) by 157 days.

(21) Appl. No.: 12/452,226

(22) PCT Filed: Jun. 17, 2008

(86) PCT No.: PCT/DK2008/050147
§ 371 (c)(1),
(2), (4) Date: Apr. 19, 2010

(87) PCT Pub. No.: WO2008/154929
PCT Pub. Date: Dec. 24, 2008

(65) Prior Publication Data
US 2010/0204664 A1   Aug. 12, 2010

(30) Foreign Application Priority Data
Jun. 21, 2007 (DK) ................................ 2007 00896
Jul. 6, 2007 (DK) ................................ 2007 01003

(51) Int. Cl.
*A61F 5/44* (2006.01)
(52) U.S. Cl.
USPC ........................................................ 604/344
(58) Field of Classification Search
USPC ........................................................ 604/344
See application file for complete search history.

(56) References Cited

U.S. PATENT DOCUMENTS

| | | | |
|---|---|---|---|
| 4,372,303 A | 2/1983 | Grossmann et al. | |
| 4,551,490 A | 11/1985 | Doyle et al. | |
| 4,710,182 A | 12/1987 | Bryson | |
| 4,826,495 A * | 5/1989 | Petersen | 604/333 |
| 5,384,174 A | 1/1995 | Ward et al. | |
| 5,545,154 A * | 8/1996 | Oberholtzer | 604/336 |
| 6,248,915 B1 | 6/2001 | Ito et al. | |
| 6,312,415 B1 * | 11/2001 | Nielsen et al. | 604/342 |
| 6,458,886 B1 * | 10/2002 | Nielsen et al. | 524/526 |
| 6,764,474 B2 * | 7/2004 | Nielsen et al. | 604/344 |
| 7,214,217 B2 * | 5/2007 | Pedersen et al. | 604/333 |
| 7,259,190 B2 * | 8/2007 | Lykke | 521/146 |
| 7,651,485 B2 * | 1/2010 | Fattman | 604/344 |
| 7,862,878 B2 * | 1/2011 | Stroebech et al. | 428/137 |
| 8,076,528 B2 * | 12/2011 | Lam et al. | 602/56 |

(Continued)

FOREIGN PATENT DOCUMENTS

| | | | |
|---|---|---|---|
| AU | 2004277821 A1 * | 9/2004 | ............. A61K 47/32 |
| AU | 2004/277821 | * | 4/2005 |

(Continued)

*Primary Examiner* — Susan Su
*Assistant Examiner* — Guy K Townsend
(74) *Attorney, Agent, or Firm* — Jacobson Holman PLLC

(57) ABSTRACT

A body waste collecting device for attachment to the body comprising a collecting pouch comprising a first wall and a second wall, the pouch being attached to an adhesive wafer, wherein a central portion of the wafer constitutes a part of the first wall of the pouch, the wafer comprises a permeable backing layer, at least one layer of an absorbent adhesive layer wherein the wafer comprises a moisture impermeable layer at least in the central portion.

20 Claims, 2 Drawing Sheets

(56) References Cited

U.S. PATENT DOCUMENTS

| | | | |
|---|---|---|---|
| 2004/0065232 A1* | 4/2004 | Lykke | 106/680 |
| 2004/0102744 A1* | 5/2004 | Fattman | 604/344 |
| 2005/0065486 A1* | 3/2005 | Fattman | 604/332 |
| 2005/0282977 A1* | 12/2005 | Stempel et al. | 525/477 |
| 2008/0311396 A1 | 12/2008 | Hamada et al. | |
| 2009/0148661 A1* | 6/2009 | Stroebech et al. | 428/137 |
| 2010/0016820 A1* | 1/2010 | Lam et al. | 604/344 |
| 2010/0113999 A1* | 5/2010 | Lam et al. | 602/79 |
| 2010/0191201 A1* | 7/2010 | Bach et al. | 604/336 |
| 2010/0191204 A1* | 7/2010 | Bach et al. | 604/344 |
| 2010/0198176 A1* | 8/2010 | Stroebech et al. | 604/344 |
| 2010/0204664 A1* | 8/2010 | Bach et al. | 604/344 |
| 2010/0204665 A1* | 8/2010 | Stroebech et al. | 604/344 |
| 2010/0280429 A1* | 11/2010 | Bach et al. | 602/54 |
| 2011/0034890 A1* | 2/2011 | Stroebech et al. | 604/344 |
| 2011/0098665 A1* | 4/2011 | Bach et al. | 604/317 |
| 2011/0125115 A1* | 5/2011 | Anders et al. | 604/344 |
| 2011/0230850 A1* | 9/2011 | Stroebech et al. | 604/344 |

FOREIGN PATENT DOCUMENTS

| | | | |
|---|---|---|---|
| CN | 101588775 A | 11/2009 | |
| EP | 0 231 508 A1 | 8/1987 | |
| GB | 2 428 381 A | 1/2007 | |
| JP | 2004 067720 A | 3/2004 | |
| WO | WO 02/066087 A1 | 8/2002 | |
| WO | WO 2005/032401 A2 | 4/2005 | |
| WO | WO 2007/128320 A2 | 11/2007 | |
| WO | WO2007128320 A2 * | 11/2007 | C08G 77/46 |

* cited by examiner

BODY WASTE COLLECTING DEVICE

This is a national stage of PCT/DK08/050147 filed Jun. 17, 2008 and published in English, which has a priority of Denmark no. PA 2007 00896 filed Jun. 21, 2007 and Denmark no. PA 2007 01003 filed Jul. 6, 2007, hereby incorporated by reference.

BACKGROUND OF THE INVENTION

1. Field of the Invention

The invention relates to a collecting device, for attachment to the body and for collecting bodily waste.

Collecting devices for collecting bodily waste, ostomy appliances, wound or fistulae drainage bandages or devices for collecting urine are usually in the form of a receptacle, e.g. a bag, pouch or tube for receiving the waste, connected to an adhesive wafer that can be attached to the skin of the patient. The wafer is typically in the form of a backing layer coated on the skin-facing surface with an adhesive layer and the wafer may further be provided with an aperture for accommodating the body opening. The size and shape of said aperture can often be adapted individually to fit the anatomy of the patient.

One of the crucial parts of such devices is the adhesive wafer. The wafer should be able to fit leak proof around the body opening and have good adherence to the skin without unintended detachment from the skin, but at the same time the wafer should be easy to remove again without damaging the skin. Furthermore, the wafer should be able to follow the movements of the body and be comfortable to wear. The adhesive and the backing layer determine these properties.

When designing a skin adhesive wafer for use in collecting devices, a major issue is to keep the skin relatively dry underneath the adhesive in order to prevent maceration. Maceration occurs when skin is unable to get rid of moisture from transpiration and results in degradation of the skin's barrier function and in bad adhesion.

Usually, skin adhesive keeps the skin dry by being moisture permeable. This allows moisture to be transported through the adhesive from the skin side to the upper side (opposite to the skin), where it is allowed to evaporate. However, this mechanism cannot be used for skin adhesives for collecting bodily waste, as in this case, the upper side of the adhesive is covered by a collecting pouch or is exposed to the inside of the pouch with a relative humidity close to 100%. Therefore, adhesives for attaching a pouch for collecting bodily waste are made water absorbent. Absorbing particles or hydrocolloids (HC) are mixed into an adhesive matrix to absorb moisture from the skin and thereby keep the skin relatively dry. This technique is well known in the art, see for example U.S. Pat. No. 4,551,490 and forms the basis for most of the commercially available ostomy adhesives.

For all such devices, a moisture impermeable backing layer is covering the upper side of the adhesive to prevent moisture from bodily waste inside the collecting pouch to permeate through the backing layer and into the adhesive, filling up the adhesive absorption capacity that otherwise should have been used to absorb moisture from the skin. The backing layers are typically mono- or multi-layered structures containing polyethylene (PE) or ethylene vinyl acetate (EVA). These materials are chosen because they are cheap and they have welding properties enabling a pouch or a coupling ring for a pouch to be welded onto the adhesive wafer. The required mechanical properties of these layers have primarily been that they should have a tensile strength being high enough to withstand the peeling force of the adhesive when removing the wafer.

Efforts have been put into finding a softer film, such that the total device is more able to stretch with the skin substrate of the wearer and thus obtain a more comfortable product. However, absorbing adhesives such as hydrocolloid adhesives are all relatively thick and are stiff adhesives, thus, using a softer film will not influence much on the softness and flexibility of the adhesive wafer, as it mainly will be the softness of the adhesive that defines the softness of the total adhesive wafer and not the softness of the backing film.

With recent development in soft absorbing adhesives, the softness of the backing film has become much more important. At present, it is no longer the softness of the adhesive that sets the lower bar for the softness of the adhesive wafer, but also the backing layer and this puts new constraints on how soft such a layer needs to be.

Thus, when working with wafers with soft adhesives, there are two essential mechanical requirements on the backing layer: It should be soft during wear, i.e. be able to handle small deformations from body movements of about 0-20% and have sufficient tensile strength to carry the peel load from removing the collecting device.

The need for a softer film at small deformations that still has high tensile strength has rendered existing film material less suitable for use as backing layer for such devices. Conventional backing layers can be made thinner to make them softer, but this reduces the tensile strength of the layer to below the strength required for removal. Films with satisfying properties have to be found in other types of materials, these materials can be moisture permeable and the problem of backflow of moisture from the pouch through the backing layer into the absorbing adhesive may suddenly become a problem.

2. Description of the Related Art

Most conventional collecting devices use impermeable backing layers to solve the problem of moisture flowing from the output in the pouch into the absorbing adhesive.

Other conventional adhesive wafers use open non-woven materials as backing layer, but weld the pouch wall to the non-woven in the whole centre portion of the adhesive wafer. This stops moisture from flowing into the adhesive from the pouch, but it also reduces the flexibility of the adhesive wafer, as the pouch material is rigid compared to the non-woven.

Thus, there is still a need for a soft and flexible collecting device having a controlled permeability to moisture.

SUMMARY OF THE INVENTION

The present invention aims at providing a body waste collecting device, which improves the patient's comfort and eliminates or—at least to a large extent—reduces the risk of skin irritation or skin damage, which may occur in the area around the body opening of a patient.

One object of the invention is to provide a collecting device, wherein moisture is prevented from passing from the pouch to the absorbing adhesive.

Another object of the invention is to provide a soft and flexible attachment to the body of the user.

BRIEF DESCRIPTION OF THE DRAWINGS

The invention is disclosed more in detail with reference to the drawings in which FIG. 1 discloses an embodiment of the collection device according to the invention and FIG. 2 discloses another embodiment of the invention.

DETAILED DESCRIPTION OF THE PRESENT INVENTION

Figure 1:
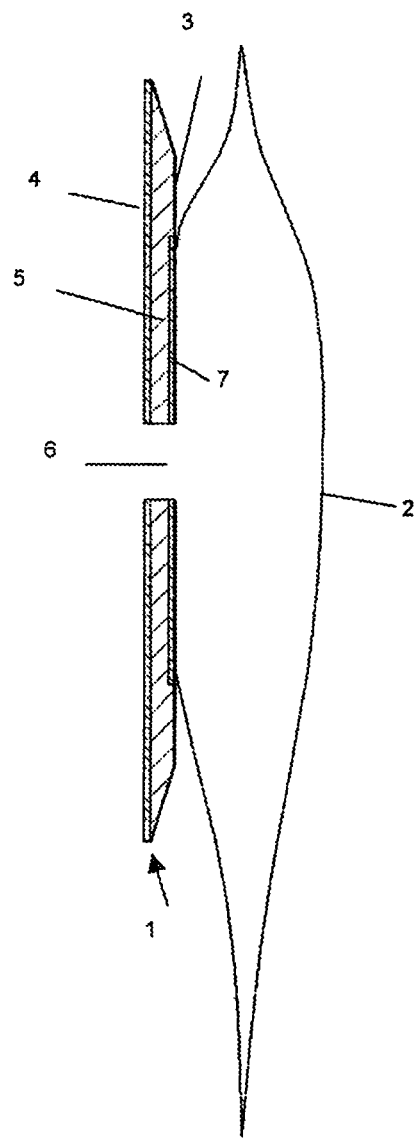

The invention relates to a body waste collecting device for attachment to the body comprising a collecting pouch comprising a first wall and a second wall, the pouch being attached to an adhesive wafer, wherein a central portion of the wafer constitutes a part of the first wall of the pouch, the wafer comprises a permeable backing layer, at least one layer of absorbent adhesive, wherein the wafer comprises a moisture impermeable layer at least in the central portion.

By body waste collecting device is meant a device being able to collect and hold the output in a collecting item for a predefined time. The fixation of the device to the skin may be obtained by a skin adhesive and the collection of body waste may be obtained by a bag.

It has surprisingly been shown that by providing the wafer of a collecting device with a layer of moisture impermeable material, preferably located between the absorbing adhesive and the semi-permeable backing layer, a soft adhesive wafer with high tensile strength can be made without backflow of moisture into the adhesive.

The invention combines the mechanical properties of a moisture permeable film with the moisture impermeable and mechanical characteristics of a soft layer, thus achieving a soft moisture impermeable adhesive wafer with high tensile strength.

By permeable layer is meant a layer where the MVTR is higher than 100 $g/m^2/24$ h as measured using the method disclosed herein.

By impermeable layer is meant a layer where the MVTR is lower than 20 $g/m^2/24$ h as measured using the method disclosed herein.

By soft moisture impermeable layer (barrier layer) is meant a moisture impermeable layer with a tensile strength at 20% strain of less than 0.25N/4 mm using the method disclosed herein.

By high tensile strength of backing layer is meant a backing layer with a maximum tensile strength of more than 2.5N/4 mm.

By soft backing layer is meant a backing layer with a tensile strength at 20% strain of less than 0.75N/4 mm using the method disclosed herein.

The use of a soft adhesive in a collecting device of the present invention provides completely new features to the user. Contrary to the traditional adhesive wafers comprising hydrocolloid adhesive, which is relatively stiff, the device according to the invention will provide the user with greater comfort as well as lower risk of leakage. A device comprising such soft adhesive in combination with a low-modulus backing layer provides an excellent attachment to the body.

However, when using a soft adhesive combined with the use of a soft and thin backing layer, such layers will be permeable to moisture. As the humidity inside the pouch is 100%, the moisture may travel from the pouch through the adhesive backing to the absorbing adhesive. This absorption of moisture from the pouch will reduce the absorption capacity that otherwise should be used for absorbing moisture from the skin.

By providing the wafer with an impermeable barrier layer, the moisture cannot pass from the pouch through the central portion of the adhesive wafer to the skin and the problem of moisture passing in the reverse direction is avoided.

In one embodiment of the invention, the barrier layer extends only to central portion of the wafer. By central portion is meant the area of the wafer surface being inside the pouch. In this way, the area of the adhesive wafer that is not inside the pouch may permeate moisture through the adhesive wafer and out into the surroundings and thus prolong the adhesive's wear time.

In one embodiment of the invention, the barrier layer extends to the total area of the wafer making the wafer easier to produce. Further, this may improve the overall mechanical properties of the entire adhesive wafer.

The thickness of the barrier layer may vary from 5 um to 1000 um as long as the layer is impermeable to moisture and does not make the wafer too rigid.

The barrier layer is preferably placed in between the permeable backing layer and the absorbing adhesive.

The barrier layer may be a separate film, an adhesive layer or a coating or it may be sprayed on the backing film.

The barrier layer may preferably be a thermoplast or a thermoset. Examples of such are tri-block copolymers like SIS (styrene isoprene styrene block copolymer), SEBS (styrene ethylene butylene styrene block copolymer) or block copolymers like EMA (ethylene-methyl acrylate), EVA (ethylene vinyl acetate), and EBA. The film may also be natural rubber or synthetic rubber like PIB (polyisobutylene) or PB (polubutylene). Mixtures of the above may also be used. Further, resins, oils and plastizicers may be added in order to design the mechanical properties of the barrier layer.

In one embodiment of the invention, the peripheral portion of the wafer is outside the pouch.

In another embodiment of the invention, the moisture impermeable layer is extending to the peripheral portion of the wafer. The barrier layer may be of the same size as the backing layer.

In an embodiment of the invention, the barrier layer is covering the area of the wafer being inside the pouch, the central portion of the wafer. Thus, the peripheral portion of the wafer being outside the pouch may not be covered with the barrier layer.

Defining inside and outside the pouch: The pouch is attached to the wafer by means of a coupling or by direct welding to the surface of the wafer and the attachment is in a zone, typically a circular line encircling a central aperture, typically for receiving a stoma, with a diameter larger than the aperture but smaller than the circumference of the wafer. The central area, being between attachment line and aperture, will be inside the pouch and the peripheral area, being between the circumference and the attachment zone, is outside the pouch.

The adhesive wafer of the device of the invention may have different shapes, such as circular, oval, square or user defined shape and the same applies for the attachment zone as well as the aperture.

In a preferred embodiment of the invention, the moisture impermeable layer is located between the backing layer and the adhesive layer.

In one embodiment of the invention, the moisture impermeable layer is located on top of the backing layer, which is on the side of the backing layer facing away from the skin.

The moisture impermeable layer may be in the form of a film or the moisture impermeable layer may alternatively be in the form of a coating.

The adhesive wafer may comprise a layer of low-absorbent adhesive. In a preferred embodiment of the invention, the low-absorbent adhesive layer is the skin-contacting layer and preferably comprises a low-absorbent, liquid impermeable, moisture permeable adhesive composition.

By low-absorbent means the adhesive should only be able to absorb a small amount of moisture in order to maintain its adhesive properties when exposed to moisture. The weight gain of the adhesive from its dry state to its equilibrium state with saline water should be less than 8%, preferably less than 4%, determined using the method disclosed herein. Otherwise, the peel force drops too much if the adhesive absorbs moisture.

In one embodiment of the invention, the moisture impermeable layer is an adhesive layer.

It is preferred that the moisture impermeable layer does not increase the mechanical stiffness of the adhesive wafer.

An advantage of the device according to the described embodiment is that it maintains its integrity upon contact with fluid. In this context, it should be noted that if the opening of the device is too small, it could be made larger by punching or cutting in order to adapt its size to the stoma. Conventional fastening arrangements for stoma bags are often provided with cutting marks, for example in the form of helical lines, to make this kind of adaptation easier. Such adaptation of size is important for ensuring that the smallest possible area of skin around the stoma comes into contact with the intestinal content collected in the stoma bag. As already mentioned, the shapeability of the device means it is easy to finely adjust the shape of the opening, in a way that this coincides with the cross-sectional shape of the stoma, which may deviate from a circular shape.

The backing layer of the device of the present invention is preferably in the form of a polymer film, coating, laminate, textile or non-woven. The backing layer is preferably a highly flexible film, being strong enough for attachment of e.g. couplings and/or pouch and for removing the device in one piece, but soft enough to follow the movements of the body.

A preferred backing layer is a polyurethane film.

Preferably, the backing layer has thermoplastic elements that enable welding of e.g. a pouch or coupling ring to the adhesive wafer. Preferred thickness of the backing layer is between 15-60 μm in order to maintain the softness of the adhesive wafer.

The device of the present invention is soft and comfortable to wear, having a good adhesive tack, but is yet easy and gentle to remove and is permeable to moisture, thus overcoming the drawbacks of the hydrocolloid adhesive devices. The adhesive is resistant to erosion and does not loose its tack when exposed to moisture.

The absorbent adhesive as well as the optional low-absorbent adhesive of the wafer may be any suitable soft adhesive being liquid impermeable but moisture permeable. Preferred adhesive are soft gel adhesives, such as silicone or polyurethane adhesives. An especially preferred adhesive is a polyalkyleneoxide polymer and an organosiloxane based cross-linked adhesive system.

A liquid impermeable, moisture permeable layer is a layer that does not allow liquid to penetrate through the layer, but allows moisture to permeate through the layer.

In a preferred embodiment of the invention, the adhesive comprises ethylene vinyl acetate.

The adhesive comprising ethylene vinyl acetate may suitably be an adhesive known in the art such as the adhesive composition disclosed, for example in Danish Patent Application No. PA 2007 01003.

In a preferred embodiment of the invention, the adhesive comprises polyacrylate.

In a preferred embodiment of the invention, the adhesive wafer comprises the combination of an adhesive comprising a polyalkyleneoxide polymer and an organosiloxane based cross-linked adhesive system and a low modulus backing layer. The soft construction facilitates easy adaptation to scars, irregularities and skin-folds. The device may be removed with minimal pain due to extreme flexibility and no skin cells are stripped off and thus no traumatisation of the skin occurs. The soft adhesive has a broad peel front and good tenancy during use. Reposition of the adhesive is also possible without loss of tack.

A soft backing layer is also preferred in order for the adhesive wafer to follow the movements of the body. The backing layer of the device according to the invention has preferably a force below 0.75 N/2.5 cm at 20% extension, preferably less than 0.5 N/2.5 cm, as measured using the technique described herein.

By low-modulus backing layer is meant a backing layer that has a force below 0.75 N/4 mm at 20% extension, preferably less than 0.5 N/4 mm, as measured using the technique described herein.

Another important property of the device of the invention is that the adherence force of the soft adhesive used does not change with time, or changes only to a small extent with time, during wear time of the device.

The adhesive wafer may comprise a layer of non-absorbent adhesive. The adhesive wafer may comprise a laminate of two or more adhesive layers with different properties. By different properties is meant e.g. absorption, permeability or mechanical properties. The first adhesive layer may be absorbent while the second may be non- or low-absorbent. The absorbency of the adhesive may be achieved by incorporating absorbent material in the adhesive, e.g. in the form of absorbent particles or salt.

It is preferred that the low-absorbent adhesive layer is on the skin-facing surface. Having a thin layer of low-absorbent adhesive facing the skin combined with another layer of absorbent adhesive facing the backing layer provides a skin-friendly attachment to the skin being capable of transporting moisture away from the skin and into the absorbing layer.

The adhesive used in the device of the present invention has a high moisture vapour transmission rate, preferably a MVTR over 100 $g/m^2/24$ hrs, which makes it breathable and very skin friendly. The high moisture transmission of the adhesive is a particular advantage, where a medical device has to be worn on the skin for a long time, e.g. days.

As used herein a water vapour permeable hydrophobic polymer means a polymer that absorbs less than 5% in wt, preferably less than 1%, at equilibrium and has a moisture vapour transmission rate of greater than 100 $g/m^2/24$ hrs, preferably greater than 200 $g/m^2/24$ hrs.

As used herein a cross-link means a small region in a macromolecule (polymer chain structure) from which more than 2 chains emanate.

The adhesive layer of the device of the invention may in a preferred embodiment of the invention comprise a polyalkyleneoxide polymer and an organosiloxane based cross-linked adhesive system.

According to one embodiment of the invention the adhesive layer of the wafer comprises the reaction product of:
(i) a polyalkyleneoxide polymer having one or more unsaturated end groups, and
(ii) an organosiloxane comprising one or more Si—H groups,
carried out in the presence of an addition reaction catalyst.

According to another embodiment of the invention, the adhesive composition of the device comprises more than 90% w/w of the polyalkylene oxide polymer that consists of polymerised alkyleneoxide moities having three or more carbon atoms.

According to another embodiment of the invention, the adhesive composition of the device comprises the reaction product of:
(i) a polyalkyleneoxide polymer having at least two unsaturated end groups, and wherein more than 90% w/w of the polyalkylene oxide polymer consists of polymerised alkyleneoxide moities having three or more carbon atoms, (ii) a polysiloxane cross-linking agent comprising 3 or more Si—H groups and optionally (iii) a polysiloxane chain extender comprising up to 2 Si—H groups carried out in the presence of an addition reaction catalyst.

According to a preferred embodiment of the invention, the addition reaction catalyst is a Pt vinyl siloxane complex.

According to a preferred embodiment of the invention, the polyalkylene oxide polymer is polypropyleneoxide.

According to a further preferred embodiment of the invention, the weight percent of polyalkylene oxide in said reaction product is 60% or above.

The polyalkylene oxide polymer having one or more unsaturated groups may be branched or linear.

However, suitably, the polyalkylene oxide polymer is linear and has two unsaturated end groups.

In one particular embodiment of the invention, the polyalkylene oxide polymer is polypropyleneoxide.

The polypropylene oxide having unsaturated end groups may be a compound of formula

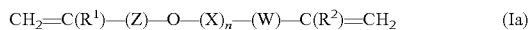  (Ia)

or

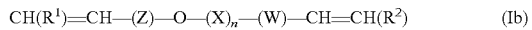  (Ib)

wherein $R^1$ and $R^2$ are independently selected from hydrogen and $C_{1-6}$-alkyl;
Z and W is $C_{1-4}$-alkylene;
X is —$(CH_2)_3$—O— or —$CH_2$—$CH(CH_3)$—O—; and
n is 1-900, more preferred 10-600, or most preferred 20-600.

The number average molecular weight of the polyalkylene oxide having unsaturated end groups is suitably between 500 and 100.000, more preferred between 500 and 50.000 and most preferred between 1.000 and 35.000.

Polypropylene oxide having unsaturated end groups may be prepared as described in U.S. Pat. No. 6,248,915 and WO No. 05/032401 or analogously to the methods described therein. Other polyalkylene oxide polymers may be prepared analogously.

The polysiloxane cross-linking agent comprising 3 or more Si—H groups is suitable a compound having the formula

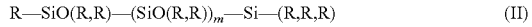  (II)

wherein at least three of the groups R are hydrogen and the rest of the groups R are each independently selected from $C_{1-12}$-alkyl, $C_{3-8}$-cycloalkyl, $C_{6-14}$-aryl, and $C_{7-12}$-arylalkyl; and m is 5-50, or preferably 10-40. The number average molecular weight as determined by GPC is suitably 500-3.000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula

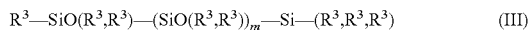  (III)

wherein up to 2 of the groups $R^3$ are hydrogen and the rest of the groups $R^3$ are each independently selected from $C_{1-12}$-alkyl, $C_{3-8}$-cycloalkyl, $C_{6-14}$-aryl, and $C_{7-12}$-arylalkyl; and m is 0-50. The number average molecular weight as determined by GPC is suitably between 200 and 65.000, most preferably between 200 and 17.500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the —$(SiO(R^3,R^3))_m$— chain of the compound of formula (II).

The polysiloxane cross-linking agent and the chain extender may be prepared as described in Japanese Patent Application No. 2002-224706 and WO No. 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, thus forming one larger compound. Addition reactions are limited to chemical compounds that have multiple-bonded atoms. Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxanes and platinum-olefin complexes, such as Pt-divinyl tetramethyl disiloxane.

The reaction is suitably carried out neat at a temperature between 25° C. and 150° C. It is not necessary to use a solvent for the reaction, which is an advantage for any adhesive, but especially for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w and more preferred below 10% w/w of the amount of polyalkylene oxide polymer having unsaturated end groups.

The cross-linking reaction does not lead to complete cross-linking of all the polyalkylene oxide polymers. The adhesive comprises a mixture of cross-linked and non cross-linked polyalkylene oxide polymer.

The adhesive composition of the device according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, and surfactants. The adhesive may also comprise pharmaceutically active ingredients. These optional ingredients may be present in the reaction mixture during the cross linking reaction.

It may be advantageous that the adhesive comprises absorbent particles. The particles may be absorbent articles such as mineral salt, hydrocolloid, microcolloids or super absorbers in order for the adhesive to absorb moisture from skin.

Preferred particle size of the absorbent particles is smaller particles, as they are more difficult to see by the naked eye and will give products that are more pleasing to the eye. An upper limit on particle size is the size of the smallest dimension of the adhesive. Thus, a 300 μm thick adhesive should not contain particles with diameters above 300 μm. There is a tendency of the hygroscopic particles to agglomerate and this effect will increase with decreasing particle size. Therefore, a preferred particle size would be from 10-300 μm. Also, the particles may contain an anti agglomerating agent to reduce agglomeration of small particles.

Microcolloid particles are well known in the art e.g. from International Patent Application No. WO 02/066087, which discloses adhesive compositions comprising microcolloid particles. The microcolloid particles may have a particle size of less than 20 microns.

Salt may be advantageous to use as absorber if it is contained within an ion impermeable matrix like the hydrophobic adhesive used in the device of this invention. Some salts like sodium chloride have an equilibrium vapour pressure of about 75% at skin temperature and will absorb water from skin and output because of the difference in vapour pressure.

In an embodiment of the invention, the adhesive comprises particles of mineral salt. The salt may be present in an amount of 1-50% w/w, more preferred in an amount of 5-25%.

In one embodiment of the invention, the adhesive comprises non-absorbent particles which presence may modify the rheologic properties of the adhesive.

The absorbent adhesive layer may comprise 1-40% w/w of hydrocolloid (HC), microcolloids or super absorbent particles (SAP) particles, more preferred 5-30% w/w particles.

The device of the present invention may have an absorbency of the adhesive of 0.02-0.4 g/2 h more preferred 0.05-0.25 g/2 h.

The collecting pouch may be detachable from the adhesive wafer by a coupling system or the pouch and the wafer may be integrated with the wafer, e.g. by welding. The two versions are known as one piece or two-piece appliances for ostomy.

In order to avoid rolling up of the edge portion during wear, it may be advantageous to bevel the edge portion of the wafer.

According to an embodiment of the invention, the collecting device is an ostomy appliance.

According to another embodiment of the invention, the collecting device is a faecal collecting device.

According to another embodiment of the invention, the collecting device is a fistula collecting device.

DESCRIPTION OF THE PREFERRED EMBODIMENTS

The invention is now explained more in detail with reference to the drawings showing preferred embodiments of the invention.

In FIG. 1 is shown a collecting device according to the invention comprising a collecting pouch (2) welded to an adhesive wafer (1). The adhesive wafer (1) comprises backing layer (3) in the form of a 25 μm thick soft backing layer with high tensile strength in the form of a polyurethane film, welded to the collecting pouch (2) on one surface and coated with an adhesive layer on the other surface. The adhesive construction is a two-layer construction comprising two layers of polyalkyleneoxide polymer and organosiloxane based cross-linked adhesive. The layer adjacent to skin (4) contains no absorbing filler whereas the second layer (5) contains 20 wt % NaCl for moisture absorption. A third layer, the barrier layer (7), in the form of an impermeable and non-absorbing layer covers at least the central portion of the wafer (1). This third layer (7) is located between the polyurethane film (3) and the NaCl containing adhesive (5). The impermeable layer (7) prevents moisture from penetrating into the NaCl containing adhesive layer (5) during use from the backside of the wafer (through the polyurethane film). The third layer (7) is in the form of a 100 my soft low permeable Styrene-Isoprene-Styrene, resin or oil adhesive formulation.

The skin adhesive surface is covered with a release liner system protecting the adhesive prior to use. The NaCl containing adhesive has a thickness of 0.8 mm and the skin adhesive side has a thickness of 0.2 mm. The total thickness of the product is approximately 1 mm thick. In order to avoid edge rolling the adhesive wafer is bevelled from 1 mm to a thickness of 0.3 mm at the rim. The adhesive wafer has an output-receiving hole of 10 mm that can be enlarged with conventional means, preferably a pair of scissors. The diameter of the wafer is 100 mm.

Figure 2:
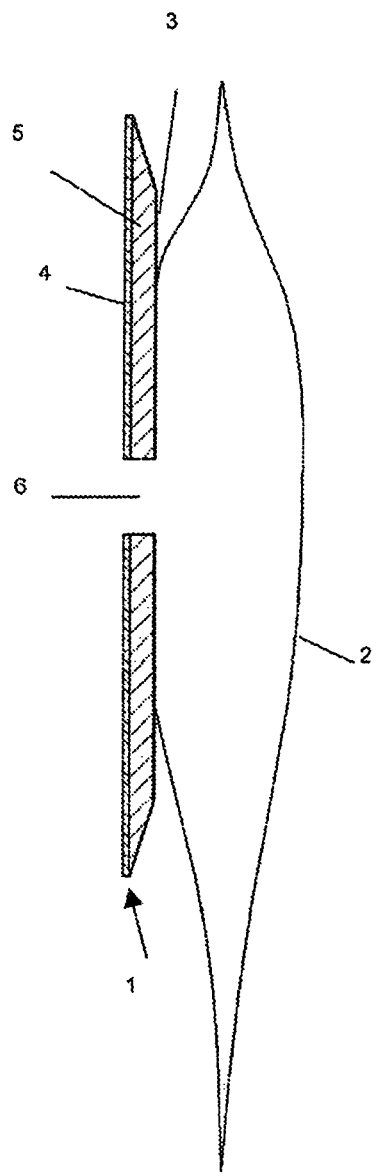

FIG. 2 discloses a collecting device with an adhesive wafer (1), the device comprising a collecting pouch (2) welded to the adhesive wafer (1). The adhesive wafer (1) comprises a backing layer (3) in the form of a 25 μm thick soft backing layer with high tensile strength in the form of a polyurethane film, welded to the collecting pouch (2) on one surface and coated with an adhesive construction on the other surface. The adhesive construction is a two-layered construction comprising two layers of polyalkyleneoxide polymer and organosiloxane based cross-linked adhesive. The layer adjacent to skin (4) contains no absorbing filler whereas the second layer (5) contains 20 wt % NaCl for moisture absorption. The adhesive surface facing the skin may be covered with a release liner system (not shown) protecting the adhesive prior to use. The layer of NaCl containing adhesive (5) has a thickness of 0.8 mm and the layer of skin facing adhesive (4) has a thickness of 0.2 mm. The total thickness of the wafer is approximately 1 mm thick. In order to avoid edge rolling the adhesive wafer is bevelled from 1 mm to a thickness of 0.3 mm along the edge portion. The adhesive wafer is provided with an aperture (6) of a diameter of 10 mm that can be enlarged into desired shape and size with conventional means, preferably a pair of scissors. The diameter of the wafer is 100 mm.

The soft backing layer with high tensile strength has tensile strength of 5 N/4 mm and a tensile strength at 20% strain of 0.43 N/4 mm using the method disclosed herein.

METHODS

Determination of Water Absorption

In order to get better correlation between measured water absorption and actual performance in a humanlike environment, a modified version of the ISO 62 standard was used: Pieces of adhesive of 1×25×25 mm$^3$ were fastened on a piece of glass using double sided adhesive and the constructs were immersed in saline water (0.9% NaCl in demineralised water) at 32° C. After 24 hours, the samples were removed and carefully dripped dry and weighed. The change in weight was recorded and reported as weight gain in percent of the original dry weight of the adhesive.

Determination of Moisture Vapour Transmission Rate (MVTR) of Barrier and Backing Layer MVTR was measured in grams per square meter (g/m$^2$) over a 24 hours period using an inverted cup method. A container or cup being water and water vapour impermeable and having an opening was used. 20 ml saline water (0.9% NaCl in demineralised water) was placed in the container and the opening was sealed with the test sample in the form of a film sheet. The container, with a duplicate, was placed into an electrically heated humidity cabinet and the container or cup was placed upside down in a way that the water was in contact with the adhesive. The cabinet was maintained at 37° C. and 15% relative humidity (RH). After about an hour, the containers were considered to be in equilibrium with the surroundings and were weighed. 24 h after the first weighing, the containers were weighed again. The difference in weight is due to evaporation of vapour transmitted through the adhesive film. This difference was used to calculate the Moisture vapour transmission rate or MVTR. The MVTR was calculated as the weight loss after 24 h divided by the area of the opening in the cup (g/m2/24 h). The MVTR of a material is a linear function of the thickness of the material. Thus, when measuring MVTR, it is important to use the correct thickness corresponding to the thickness of the film in the device.

Determination of Mechanical Properties of Backing and Barrier Layer

For measuring softness of the layer, the testing guidelines from standard ISO527-1 were used. However, the parameters defined in ISO527-1 are in it self not sufficient to exactly describe the relevant parameters for ostomy devices. An ostomy device is placed on the stomach, on skin that can easily deform more than 20%. The relevant deformation for a soft adhesive wafer with a soft backing is in the same magnitude and we have therefore defined softness (modulus) of adhesive wafer components as the force in Newton at 20% deformation divided by initial sample width. We used 'dog-bone' test specimens similar to the ones described in ISO 527-2 FIG. 1, but with different dimensions to accommodate the fact that some adhesive wafers are too small to be tested with ISO 527-1. We used test samples analogue to the samples from ISO527.2 FIG. 1, but where the width $b_1$ of the narrow portion was 4 mm and Gauge length $L_0$ was 10 mm. Relative deformation E was calculated as the absolute deformation $\Delta L$ divided by the initial length $L_0$ as described in ISO 527-1. The rate of deformation was set to 1 mm/s. Tensile strength is measured as the maximum obtained force and is reported in N/4 mm. To accommodate the fact that some layers are isotropic, samples were measured in the softest direction. The obtained values are averages of at least 3 measurements.

The invention claimed is:

1. A body waste collecting device for attachment to the body comprising
   a) a collecting pouch having a first wall and a second wall and
   b) an adhesive wafer having a central portion that is part of the first wall of the pouch, the adhesive wafer comprising
      a permeable backing layer having a MVTR higher than 100 g/m$^2$/24 h,
      at least one adhesive layer, the adhesive layer being soft, absorbent, and moisture permeable, and
      a moisture impermeable layer at least in the central portion of the wafer and located either between the adhesive layer and the backing layer or on top of the backing layer,
   wherein moisture is prevented from passing from the pouch to the adhesive layer.

2. The device according to claim 1, wherein the backing layer is soft with high tensile strength.

3. The device according to claim 1, wherein the backing layer has a low-modulus and is in the form of a polymer film, coating, laminate, textile, or non-woven.

4. The device according to claim 1, wherein the backing layer has a low-modulus and a force below 0.75 N/4 mm at 20% extension.

5. The device according to claim 1, wherein the backing layer has a low-modulus and a force below 0.5 N/4 mm at 20% extension.

6. The device according to claim 1, wherein the adhesive layer comprises a silicone, polyurethane, or polyacrylate based adhesive.

7. The device according to claim 1, wherein the adhesive layer comprises a polyalkyleneoxide polymer and an organosiloxane based cross-linked adhesive system.

8. The device according to claim 1, wherein the adhesive layer comprises ethylene vinyl acetate.

9. The device according to claim 1, wherein the peripheral portion of the wafer is outside the pouch.

10. The device according to claim 1, wherein the moisture impermeable layer extends to the peripheral portion of the wafer.

11. The device according to claim 1, wherein the moisture impermeable layer has a MVTR lower than 20 g/m$^2$/24 h.

12. The device according to claim 1, wherein the moisture impermeable layer is in the form of a film.

13. The device according to claim 1, wherein the moisture impermeable layer is in the form of a thermoplastic film.

14. The device according to claim 1, wherein the moisture impermeable layer is in the form of a coating.

15. The device according to claim 1, wherein the moisture impermeable layer is an adhesive layer.

16. The device according to claim 1, wherein the wafer comprises a layer of non-absorbent adhesive.

17. The device according to claim 1, wherein the collecting device is an ostomy appliance.

18. The device according to claim 1, wherein the collecting device is a faecal collecting device.

19. The device according to claim 1, wherein the collecting device is a fistula collecting device.

20. The device according to claim 1, wherein the moisture impermeable layer is only in the central portion of the wafer.

* * * * *